United States Patent [19]

Gilman et al.

[11] Patent Number: 5,005,567

[45] Date of Patent: Apr. 9, 1991

[54] METHOD FOR TREATING LEG WOUNDS

[75] Inventors: Thomas H. Gilman, Mansfield; Betsy C. Westlake, Norton, both of Mass.

[73] Assignee: The Kendall Company, Mansfield, Mass.

[21] Appl. No.: 397,606

[22] Filed: Aug. 24, 1989

[51] Int. Cl.$^5$ ............................................... A61F 13/00
[52] U.S. Cl. .......................................... 128/165; 2/240
[58] Field of Search ...................... 128/165, 882, 892; 2/239, 240, 241, 242

[56] References Cited

U.S. PATENT DOCUMENTS

| | | | |
|---|---|---|---|
| 2,169,203 | 8/1939 | Hinchliff | 128/165 |
| 2,574,873 | 11/1951 | Jobst | 128/165 |
| 2,646,797 | 7/1953 | Scholl | 128/165 |
| 3,728,872 | 4/1973 | Hartigan et al. | 128/165 |
| 3,856,008 | 12/1974 | Fowler et al. | 128/165 |
| 3,874,001 | 4/1975 | Patience et al. | 2/240 |
| 3,889,494 | 6/1975 | Patience et al. | 66/189 |
| 4,015,448 | 4/1977 | Knohl | 66/187 |
| 4,021,860 | 5/1977 | Swallow et al. | 2/239 |
| 4,027,667 | 6/1977 | Swallow et al. | 2/240 |
| 4,069,515 | 1/1978 | Swallow et al. | 2/239 |
| 4,180,869 | 1/1980 | Pedergrass et al. | 2/240 |
| 4,424,596 | 1/1984 | Jackson | 2/240 |
| 4,513,740 | 4/1985 | Westlake | 128/165 |
| 4,745,917 | 5/1988 | Hasty et al. | 128/165 |
| 4,811,727 | 3/1989 | Etienne | 128/165 |

*Primary Examiner*—Stephen C. Pellegrino
*Assistant Examiner*—Michael Rafa
*Attorney, Agent, or Firm*—Alvin Isaacs

[57] ABSTRACT

Method for treating leg wounds requiring both bandaging and the application of compressive pressure wherein a dressing is applied to cover the wound and an elastic stocking is put on to provide the compressive pressure; the improvement wherein a loosely knit stocking which easily slips on is first put on over the dressing and then the elastic stocking, the coefficient of friction between the stockings being relatively low, thereby greatly facilitating putting on the elastic stocking.

17 Claims, No Drawings

METHOD FOR TREATING LEG WOUNDS

BACKGROUND OF THE INVENTION

This invention relates to a novel bandaging system and, more particularly, to the treatment of wounds such as exuding leg ulcers, for which the treatment protocol requires bandaging and the application of compressive pressure.

Since the invention is particularly directed to the treatment of leg ulcers, it will be best understood by reference thereto.

In general, the treatment regimen for leg ulcers includes the combination of the application of a medicament and compression.

It is well known in the art to apply a dressing known in the art as "Unna's Boot" for treatment of leg ulcers. Unna's Boot is a bandage impregnated with a paste that includes zinc oxide and gelatin and has the consistency of a soft plaster of paris bandage which does not set to a firm cast. The zinc oxide can be beneficial to the irritated skin and is often applied for this purpose.

Since the application of compressive pressure is also known to be beneficial to the treatment of leg ulcers, the Unna's Boot is wrapped under compression around the leg in the area of the ulcer.

The Unna's Boot is often overwrapped with an elastic or cohesive bandage to provide additional compression and to protect the paste bandage.

While Unna's Boot is generally useful in the treatment of leg ulcers, if applied properly, and with non-compliant patients does serve the additional function of making it extremely difficult for the patient to gain access to the ulcer and cause harm, it does suffer from certain significant disadvantages.

One major disadvantage is that it produces varying compression levels due to the human factor of individuals employing different techniques in applying the bandage. In other words, it takes a great deal of practice and skill to consistently apply the proper compression levels when wrapping the dressing.

Another problem is the inability to apply proper graduated compression levels when wrapping the dressing. Applying pressure gradients has been shown to be superior to uniform pressures when treating venous ulcers. Unna's Boot dressings inherently provide irregularities of bandage compression levels which do not retain the pressure and, consequently, one must rely on subjective application to provide a graduated compression.

Moreover, application of a Unna's Boot dressing is messy and time-consuming. The dressing should be changed at least weekly and this cannot normally be done by the patient at home. Consequently, the patient is typically required to visit a hospital or clinic on an out-patient basis to do this.

For these reasons, the clinician or practitioner has explored alternatives to the use of Unna's Boot. These include various types of primary and secondary dressings in contact with the ulcer and leg with compression applied by alternative means. One such alternative is the use of elastic bandages to apply compression. However, a basic problem with elastic bandages again is the variability of compression applied by the individual wrapping the leg. Another significant disadvantage is that the elastic bandages tend to slip due to normal movements of the patient and consequently do not retain their position as originally applied.

A possible viable solution to the problem is the use of elastic stockings such as those commercially available from The Kendall Company, assignee of the instant invention. Such stockings will provide the proper pressure gradient for treatment of the venous disorder. As illustrative of these elastic stockings, mention may be made of those described and claimed in U.S. Pat. No. 4,745,917 issued to James H. Hasty.

However, elastic stockings are not usually employed with ulcers that have not healed, since the stockings are difficult to apply over a dressing and may stain with ulcer exudate unless additional absorbent materials are placed over the primary dressing. On the other hand, the use of a primary dressing with an overlying absorbent secondary dressing further materially increases the difficulty in putting on the elastic stocking over these primary and/or secondary dressings.

In summary, from the standpoint of applying the proper compression and the ease of doing so, the use of the known elastic stockings offers the best approach to providing the compression for treating leg ulcers. However, the difficulty in putting the stocking on over the dressing applied to the unhealed ulcer makes their use for treating unhealed ulcers generally impractical.

It is to this problem that the present invention is directed. Stated simply, the task of this invention can be stated to be to find a practical way to use the known elastic stocking technology in combination with a dressing for treatment of venous leg ulcers.

BRIEF SUMMARY OF THE INVENTION

In accordance with this invention, the task is solved in an elegant manner by employing a "two-stocking" system wherein a first stocking which may simply be termed a "slippery stocking" is first put on over the dressing, followed by the elastic stocking providing the compression, the "slippery stocking" slipping easily over the dressing and leg and possessing a sufficiently low coefficient of friction, as will be detailed hereinafter, such that the elastic stocking in turn is easily applied thereover.

DETAILED DESCRIPTION OF THE INVENTION

As was heretofore mentioned, the standard treatment for ulcers which have not healed, i.e. produce exudate, utilizes the combination of a dressing and compressive pressure.

For the reasons previously discussed, it is most desirable to provide the requisite compression by employing a compression stocking over the dressing. However, they are difficult to apply over the dressing and consequently do not find favor in the therapeutic treatment of leg ulcers.

In accordance with this invention the task of rendering the use of compression stockings feasible is solved in an efficient and elegant manner by employing what may be termed a "two-stocking" system wherein a first stocking having a low co-efficient of friction is first applied over the dressing, and the compression stocking is then slipped over the first stocking (designated for purposes of simplicity as a "slippery stocking").

This system enables one to select from a wide range of bandages and dressings. Accordingly, the selection of the particular dressing to be applied to cover the ulcer will be a matter of individual selection within the expected judgement of the skilled clinician. Accordingly, the particular dressing which may be employed per se comprises no part of this invention.

However, by way of illustration, a particularly efficacious dressing for this purpose comprises a vented absorbent dressing of the type described and claimed in the copending application of the co-applicant, Thomas Gilman, Ser. No. 337,591 filed Apr. 12, 1989, the disclosure of which is incorporated by reference herein.

In general, the dressings described and claimed in the aforementioned copending application comprise a base sheet for contacting the skin of the patient, the base sheet having an opening for placement over the wound and vent means for providing controlled leakage of fluid along a path from the wound through the opening of the base sheet. The dressing may include means for preventing bacteria from reaching the wound along the fluid path and will preferably further include means for absorbing the wound fluid passing from the vent means.

In the preferred embodiments (illustrated in FIGS. 14-22 of the aforementioned copending application) a vent or cover sheet is provided to cover the opening in the dressing adapted to be positioned over the wound. One or more channels for fluid removal are provided by having at least a portion of this cover sheet secured in raised relationship to the base sheet. In the simplest form, the cover sheet is attached to the base sheet along two lines with the intermediate portion of the cover sheet between two points of attachment being raised or elevated to define a channel through which fluid may leak. In other words, the linear dimension of the cover sheet between two attachment points will be greater than the linear dimension of the base sheet between points of attachment.

As is discussed in more detail in the aforementioned application, the vented dressings described and claimed therein provide certain significant advantages in the treatment of a draining wound, including maintaining a moist environment, prevention of scab formation, leakage of exudate in a controlled manner, inhibition of the adhesive holding the dressing to the skin being undermined by lateral diffusion of exudate, and prevention of bacteria reaching the wound.

The compression stockings which are to be employed in the practice of this invention may be any of those heretofore known in the art for applying a graduated or uniform compressive pressure to the leg, the former being preferred. As examples of such known compression stockings, mention may be made of those disclosed in the following U.S. Patents: U.S. Pat. Nos. 3,828,369; 3,874,001, 3,889,494; 4,015,448; 4,021,860; 4,027,667; 4,069,515; 4,180,869; 4,424,596; 4,513,740; and 4,745,917.

While not limited thereto, the compression stockings preferably provide a pressure gradiant for optimum beneficial results. The gradiant may, for example, provide compressive pressure in the ankle portion of the stockings of on the order of 10-50 and most preferably 30-40 mm Hg; and in the calf portion on the order of 5 to 25, preferably 12-18 mm Hg.

In any event, the foregoing discussion is by way of illustration only, it being understood that the selection of the particular elastic stocking to be employed in the practice of this invention will be within the expected judgement the skilled worker in the light of the known state of the art taken in conjunction with the instant disclosure.

Irrespective of the type of bandage and/or elastic stocking desired for treatment of leg ulcers, a serious problem inherently exists in attempting to put the stocking on over the selected bandage, which problem is the essential task of this invention.

In accordance with this invention, the task is solved by first putting on over the applied dressing what may be termed a "slippery stocking" which may be further characterized as being knit sufficiently loosely so that it slips on easily over the dressing, the outer surface of this stocking and the inner surface of the compression (outer) stocking to be applied thereover having a relatively low coefficient of friction as compared to the coefficient of friction between the inner surface of the compression stocking and the leg and/or dressing over the wound.

Preferably, the knit (inner) stocking to be applied over the dressing in accordance with this invention will be made of a flat filament yarn, e.g. silk or a manmade yarn such as nylon or rayon, and will be of a denier no greater than about 40 (40 grams/9000 meters), a 30 denier stocking being found to be particularly suitable.

In the following discussion of coefficient of friction, reference is made for the sake of technical accuracy to numerical values derived from a commercially available Kawabata Evaluation System employing their FB4 surface testing instrument, the tests being made on a FB4 flat table mount fitted with a Kawabata standard FB4 friction load cell.

Since it is likely that different devices for determining the coefficient of friction may give slightly different values, it is accordingly to be expressly understood that the mean coefficient of friction (MIU) values expressed hereinafter and in the appended claims are to be construed as the values derived from the testing device employed, namely the Kawabata testing instrument previously described.

Since the MIU in the wale direction is considered to be the essential determinant in putting stocking on in the practice of this invention, the MIU in the course (horizontal row) is not considered to be critical.

With this aforementioned testing instrument, it has been determined that for improved ease in putting the compression stocking on over the inner slippery stocking, the mean coefficient of friction in the wale direction between the outer surface of the slippery stocking and the inner surface of the compression stocking should, for optimum results, be no greater than about 0.25 and preferably no greater than about 0.20. It will however be appreciated that somewhat higher values will still provide improved ease in putting on the compression stocking and are accordingly within the scope of the invention.

The following example shows by way of illustration and not by way of limitation the practice of this invention.

EXAMPLE

A sheer inner stocking in the form of a plain knit tube was prepared from flat nylon filament yarn, 30 denier, 3 filament, Z twist. Its dimensions were 22½" in length, 9½" in circumference.

An elastic compressive stocking having a gradient pressure profile of the general type described in the aforementioned U.S. Pat. No. 4,745,917 was also provided. It was a patterned knit (pique) shaped stocking, 19" long (12½" top to heel, 6½" heel to toe), 10" circumference at the top tapering to 8 12" at 5" down from top, 7" circumference at the ankle (11" down from the top). It was made of 70 denier, single ply, 17 filament nylon plus 140 denier Lycra covered with a 40 denier, 13 filament nylon; elongated warp: 25%; filling: 25%; total area: 56% increase.

Using the aforementioned Kawabata test equipment, the friction test (to determine the coefficient of friction between the outer surface of the slippery sock and the inner surface of the compression stocking) was performed to represent the layering of the compression stocking over the slippery stocking.

The Kawabata probe was covered with the compression stocking so that the inside of the compression stocking was exposed to rub against the outside of the slippery sock to simulate the condition which would take place when putting the stockings on.

The MIU (mean coefficient of friction) and MMD (mean deviation of coefficient of friction) values were determined both for the wale and for the course.

These values were:

| MIU | | MMD | |
|---|---|---|---|
| Wale | Course | Wale | Course |
| 0.179 | 0.219 | 0.008 | 0.011 |

As heretofore mentioned, only the coefficient of friction in the wale is considered critical since only the frictional force in the longitudinal direction is significant when putting on stockings. However, for the sake of completeness, the values in the course were also reported by the outside testing source engaged to perform the tests.

It is significant to note that the mean deviation was very small, indicating minimal variability for the measurements, while the respective stockings described in the foregoing example are illustrative of those contemplated by the present invention, it will be appreciated that various modifications and changes in design or structure may be made without departing from the scope of the invention as described.

For instance, by the judicious use of specific yarn and knit patterns, the stockings can be made with varying degrees of surface friction to permit easy movement of the compression stocking over the inner one.

Moreover, it is contemplated that the so-called slippery stocking may be coated or impregnated with a composition for reducing friction.

The practice of this invention contemplates the use of both above knee and below knee stockings with either open or closed toe portions.

Since certain changes may be made without departing from the scope of the invention herein involved, it is intended that all matter contained in the foregoing description be interpreted as illustrative and not in a limiting sense.

What is claimed is:

1. A method for treating leg wounds requiring both bandaging and the application of compressive pressure, comprising the steps of:
   (1) applying a dressing covering the wound;
   (2) putting a first stocking on the leg and over the wound, said stocking being characterized as being a loosely knit stocking which easily slips on the leg and over the wound; and
   (3) putting a second stocking on over said first stocking, said second stocking being an elastic stocking which applies said compressive pressure to the wound, the coefficient of friction between the outer surface of said first stocking and the inner surface of said second stocking frictionally engaging one another in putting on said second stocking being relatively low as compared to the coefficient of friction between the inner surface of said second stocking and said leg and dressing, whereby greatly to facilitate putting on said elastic second stocking to apply said compressive pressure.

2. A method as defined in claim 1 wherein said elastic stocking is of the type which applies a pressure gradient between the ankle and calf portions of the leg, the greater compressive pressure being applied to the ankle region.

3. A method as defined in claim 2 wherein said elastic stocking provides a compressive pressure in said ankle region of from about 10 to about 50 millimeters of mercury and a compressive pressure in said calf region of from about 5 to about 25 millimeters of mercury.

4. A method as defined in claim 2 wherein said elastic stocking provides a compressive pressure in said ankle region of from about 30 to about 40 millimeters of mercury.

5. A method as defined in claim 4 wherein said elastic stocking provides a compressive pressure in said calf portion of from about 12 to about 18 millimeters of mercury.

6. A method as defined in claim 1 wherein said first stocking applied first over said dressing is made of a flat filament yarn and has a denier no greater than about 40.

7. A method as defined in claim 1 wherein said dressing has vent means for providing controlled leakage of fluid from said wound along a path from said wound.

8. A method as defined in claim 7 wherein said dressing comprises a base sheet for contacting the skin around said wound, said base sheet having an opening for placement over said wound and said controlled leakage provided by said vent means is along a path from said wound through said opening.

9. A method as defined in claim 1 wherein said coefficient of friction of said first and second stockings is no greater than about 0.25.

10. A method as defined in claim 9 wherein said coefficient of friction is no greater than 0.20.

11. A method for treating leg wounds requiring applying both a dressing and compressive pressure, comprising the steps of:
   (1) applying a dressing covering the wound;
   (2) putting a first stocking on the leg and over the wound, said stocking being made of a flat filament yarn and having a denier no greater than about 40, said stocking further being characterized as being a loosely knit stocking which easily slips on the leg and over the wound; and
   (3) putting a second stocking on over said first stocking, said second stocking being an elastic stocking adapted for applying said compressive pressure to the leg, the coefficient of friction between the outer surface of said first stocking and the inner surface of said second stocking being no greater than about 0.25.

12. A method as defined in claim 11 wherein said elastic stocking is of the type which applies a pressure gradient between the ankle and calf portions of the leg, the greater compressive pressure being applied to the ankle region.

13. A method as defined in claim 11 wherein said elastic stocking provides a compressive pressure in said ankle region of from about 10 to about 50 millimeters of mercury and a compressive pressure in said calf region of from about 5 to about 25 millimeters of mercury.

14. A method as defined in claim 11 wherein said elastic stocking provides a compressive pressure in said ankle region of from about 30 to about 40 millimeters of mercury.

15. A method as defined in claim 14 wherein said elastic stocking provides a compressive pressure in said calf portion of from about 12 to about 18 millimeters of mercury.

16. A method as defined in claim 12 wherein said dressing has vent means for providing controlled leakage of fluid from said wound along a path from said wound.

17. A method as defined in claim 16 wherein said dressing comprises a base sheet for contacting the skin around said wound, said base sheet having an opening for placement over said wound and said controlled leakage provided by said vent means is along a path from said wound through said opening.

* * * * *